US011406769B2

(12) United States Patent
Törnsten

(10) Patent No.: US 11,406,769 B2
(45) Date of Patent: Aug. 9, 2022

(54) LUBRICATION OF AN INJECTION NEEDLE

(71) Applicant: Galderma Holding SA, La Tour-de-Peilz (CH)

(72) Inventor: Jonas Törnsten, Uppsala (SE)

(73) Assignee: Galderma Holding SA, Zug (CH)

( * ) Notice: Subject to any disclaimer, the term of this patent is extended or adjusted under 35 U.S.C. 154(b) by 0 days.

(21) Appl. No.: 15/114,598

(22) PCT Filed: Jan. 30, 2015

(86) PCT No.: PCT/EP2015/051910
§ 371 (c)(1),
(2) Date: Jul. 27, 2016

(87) PCT Pub. No.: WO2015/114082
PCT Pub. Date: Aug. 6, 2015

(65) Prior Publication Data
US 2016/0339185 A1 Nov. 24, 2016

(30) Foreign Application Priority Data
Jan. 31, 2014 (EP) .................................... 14153396

(51) Int. Cl.
A61L 31/02 (2006.01)
A61L 31/14 (2006.01)
(Continued)

(52) U.S. Cl.
CPC .............. A61M 5/42 (2013.01); A61L 31/02 (2013.01); A61L 31/14 (2013.01); A61M 5/32 (2013.01);
(Continued)

(58) Field of Classification Search
CPC .......... A61M 2210/04; A61M 37/0076; A61M 5/427; A61M 2005/1787; A61L 2400/10; A61L 31/44
See application file for complete search history.

(56) References Cited

U.S. PATENT DOCUMENTS 3,633,580 A * 1/1972 Knox .................. A61M 5/3286
604/274
5,186,972 A 2/1993 Williams et al.
(Continued)

FOREIGN PATENT DOCUMENTS

CA 2 093 585 C 10/1958
EP 0650699 A1 5/1995
(Continued)

OTHER PUBLICATIONS

International Search Report (PCT/ISA/210) dated Apr. 17, 2015, by the European Patent Office as the International Searching Authority for International Application No. PCT/EP2015/051910.
(Continued)

Primary Examiner — William R Carpenter
Assistant Examiner — William R Frehe
(74) Attorney, Agent, or Firm — Foley & Lardner LLP; Sunit Talapatra

(57) ABSTRACT

A method for lubricating an injection needle when used multiple times at a single occasion to penetrate a support, the method including the steps of: a) depositing a layer of a lubricating composition on the support; b) penetrating multiple times the layer of the lubricating composition deposited in step a) with the injection needle, thereby providing a lubricated injection needle having a deposited layer of the lubricating composition thereon.

19 Claims, 7 Drawing Sheets

(51) Int. Cl.
*A61M 5/32* (2006.01)
*A61M 5/42* (2006.01)
*A61M 5/178* (2006.01)

(52) U.S. Cl.
CPC .......... *A61L 2400/10* (2013.01); *A61M 5/329* (2013.01); *A61M 5/3287* (2013.01); *A61M 2005/1787* (2013.01)

(56) References Cited

U.S. PATENT DOCUMENTS

| | | | |
|---|---|---|---|
| 5,258,013 | A | 11/1993 | Granger et al. |
| 5,545,143 | A | 8/1996 | Fischell |
| 5,653,695 | A | 8/1997 | Hopkins et al. |
| 5,865,744 | A * | 2/1999 | Lemelson ............. A61M 5/427 128/922 |
| 6,015,398 | A | 1/2000 | Arimatsu et al. |
| 2001/0021832 | A1 | 9/2001 | Numao et al. |
| 2003/0114882 | A1 | 6/2003 | Roby et al. |
| 2004/0013747 | A1 * | 1/2004 | Tucker .................... A61K 9/06 424/718 |
| 2004/0082644 | A1 * | 4/2004 | Korsten ............... A61K 31/401 514/411 |
| 2005/0177117 | A1 | 8/2005 | Crocker et al. |
| 2006/0029672 | A1 | 2/2006 | Schleuning |
| 2007/0053859 | A1 * | 3/2007 | Bui ........................ A61K 8/891 424/63 |
| 2009/0155314 | A1 * | 6/2009 | Tezel ...................... A61K 8/66 424/239.1 |
| 2009/0281013 | A1 * | 11/2009 | Patel ........................ A61K 8/31 510/158 |
| 2010/0268189 | A1 * | 10/2010 | Byrnes ................. A61M 37/00 604/506 |
| 2011/0112565 | A1 * | 5/2011 | Maurer ..................... C23C 2/00 427/2.28 |
| 2011/0196195 | A1 * | 8/2011 | Raven ............... A61M 39/0208 600/37 |
| 2012/0029469 | A1 * | 2/2012 | Horvath .............. A61M 5/3213 604/506 |
| 2012/0059333 | A1 | 3/2012 | Singhal |
| 2013/0012886 | A1 | 1/2013 | Kawachi |
| 2014/0271897 | A1 * | 9/2014 | Pathak .................. A61K 47/34 514/254.11 |
| 2014/0277120 | A1 * | 9/2014 | Cichocki ................ A61L 31/10 606/222 |

FOREIGN PATENT DOCUMENTS

| | | | |
|---|---|---|---|
| EP | 2 548 597 A1 | | 1/2013 |
| JP | H06088025 | * | 9/1992 |
| JP | 06-88025 A | | 3/1994 |

OTHER PUBLICATIONS

Written Opinion (PCT/ISA/237) dated Apr. 17, 2015, by the European Patent Office as the International Searching Authority for International Application No. PCT/EP2015/051910.

Written Opinion (PCT/IPEA/408) dated Jan. 13, 2016, by the European Patent Office as the International Preliminary Examining Authority for International Application No. PCT/EP2015/051910.

International Preliminary Report on Patentability (PCT/IPEA/409) dated Apr. 19, 2016, by the European Patent Office as the International Preliminary Examining Authority for International Application No. PCT/EP2015/051910.

Dow Corning Europe SA, Life Science Technology et al., "(Trans-)dermal delivery of lidocaine from silicone topical excipients across pig skin", A.Sieg1, V. Caprasse1, S. Cornelis2, X. Thomas3, obtained from the internet on Aug. 26, 2012 (1 Pgs).

Sport Chalet, "Mission Skincare High Performance Anti-Friction Cream", Manufacturer Model No. 201000B., obtained from the internet on Aug. 16, 2012, (2 pgs).

* cited by examiner

LUBRICATION OF AN INJECTION NEEDLE

The present invention relates to the field of injection needles. The present invention further relates to a method and its use for lubricating an injection needle when used multiple times. The present invention further relates to a lubricating composition for use in the method, a kit comprising an injection needle and a lubricating composition, and a method of preparing for multiple injections and/or needle penetrations.

When using an injection needle of a syringe multiple times the treating professional often experience that the injection needle turns blunt after a number of penetrations into a support, e.g. human skin. As a consequence of the increased bluntness of the injection needle, there is a need to increase the force performed on the syringe in order for the injection needle to penetrate the surface of the support. Once the surface is penetrated, a decreased force on the syringe is needed for further penetration of the injection needle into the support. A problem experienced whilst using a blunt injection needle is that it is more difficult to perform the penetrations in a controlled way. More specifically, when a high force is needed on the syringe in order for the injection needle, attached thereto, to penetrate the surface of the support, it is difficult to timely decrease the force performed on the syringe once the injection needle penetrates the surface of the support. This causes discomfort for both the treated person and the treating professional, and may e.g. lead to bruising Today, injection needles are usually fabricated with a coated material thereon, such as a silicone-based coating. After the first use of the injection needle, the coated layer thereon starts to wear off. If the injection needle is used multiple times, the coated material may completely wear off. When using an injection needle multiple times on e.g. a patient (s)he would experience an increased pain and discomfort as the number of skin penetrations increases. Today, in order to avoid this drawback, the injection needle is exchanged after a certain number of skin penetrations. This may however be time-consuming and may increase the patient's discomfort.

A further drawback may be that a large number of injection needles is thrown away, leading to a large amount of sharp medical waste, that need to be handled. Another drawback may be the risk of needle stick when the clinician exchanges the needle.

US 2012/0059333 A1 discloses an injection needle that enables reuse of a single-use injection needle for single penetrations at separate occasions for a user. A device disclosed herein for this purpose has a needle cover with a disinfecting agent, a sanitizing agent and a lubricating agent, such as a silicone based lubricant, that are positioned inside the needle cover. The needle cover sanitizes, disinfects and lubricates the injection needle for reuse when the injection needle is moved inside the needle cover and positioned therein for temporary storage.

JP 6-88025 discloses a silicone coating composition. It is evident from the Japanese application text, e.g. the claims, that the composition is intended for use as a coating agent for lubricating metal surfaces, e.g. injection needles.

There is a need in the art for a method and/or an article which allows for use of an injection needle multiple times at a single occasion.

An object of the present invention is to provide improved and simplified methods and compositions which allow for efficient use of an injection needle multiple times at a single occasion to penetrate a support.

These objects are achieved, in a first aspect, by means of a method for lubricating an injection needle when used multiple times at a single occasion to penetrate a support, the method comprising the steps of:
 a) depositing a layer of a lubricating composition on the support,
 b) penetrating multiple times the layer of the lubricating composition deposited in step a) with the injection needle, thereby providing a lubricated injection needle having a deposited layer of the lubricating composition thereon.

The inventive method thus provides an improved and simplified process, in which the injection needle is efficiently lubricated when it is used multiple times at a single occasion. Hence, the injection needle may acquire a deposited layer of the lubricating composition thereon, such as each of the multiple times it is used. The method thus enables the injection needle to become re-lubricated each of the multiple times it is used. As a consequence of the injection needle being efficiently lubricated, the injection needle is provided with a prolonged life time and may thus be used multiple times at a single occasion without having to exchange the injection needle for a new injection needle in-between the multiple times the injection needle is used. Moreover, a further benefit of not having to exchange the injection needle as often is that it may contribute to an increased safety due to a reduced handling of the injection needle. In prior art methods, the coating on the injection needle may wear off when using the injection needle multiple times. This is what happens when it is experienced that the injection needle goes blunt after a number of penetrations. A penetration force of an injection needle, such as a required penetration force, i.e. the force needed on an injection needle for it to penetrate a support, increases as the coating of the injection needle wears off. The inventors have surprisingly found out that by efficiently keeping the injection needle lubricated when using it multiple times at a single occasion, this problem is overcome. Moreover, the required penetration force may be kept at a lower value compared to the value of the required penetration force for the injection needle which does not have an intact coating thereon, which alleviates the problem of decreasing the force immediately after penetration.

Another advantage of keeping the injection needle lubricated is that it saves time, since there is no need to e.g. discharge the injection needle in-between the multiple times it is used. This leads to a more economical and environmentally friendly way of using the injection needles. A further advantage is that conventional injection needles may be used in the inventive method.

The layer of the lubricating composition on the support may be considered as a first layer, and the deposited layer of the lubricating composition on the injection needle may be considered as a separate, second layer.

In an embodiment, step a) is performed once. In this way, the method of lubricating the injection needle when used multiple times at a single occasion to penetrate the support may efficiently be performed. In an embodiment, step a) is repeatedly performed. In this way, an intact layer of the lubricating composition on the support is ensured when the injection needle is used multiple times at a single occasion.

In an embodiment, step b) is performed at least 10 times, or even more than 10 times, such as at least 15 times. In an embodiment, step b) is performed at least 5 times, such as at least 7 times or such as at least 9 times. In an embodiment, step b) is performed at least 12 times, such as at least 17 times or such as at least 20 times. In an embodiment, step b) is performed at least 30 times, such as at least 40 times or such as at least 50 times. In an embodiment, step b) is performed at least 70 times, such as at least 100 times or such as at least 130 times. In an embodiment, step b) is performed at least 150 times, such as at least 170 times or such as at least 200 times.

In an embodiment, the lubricating composition is sterile. It may be important that the lubricating composition is sterile, in order to avoid any pathogen microorganisms.

In an embodiment, the lubricating composition is in the form of a gel, a cream, a solution, a lotion, a dispersion, an ointment, a paste, a salve or an embrocation. Preferred forms for the composition are a gel or a cream.

In an embodiment, the lubricating composition may have a relative high viscosity at room temperature, such as within a range of from 1 to 200 Pa·s, or such as within a range of from 5 to 100 Pa·s. An advantage of this embodiment is that the lubricating composition stays approximately within the area on the support where it has been deposited.

In an embodiment, the amount of the layer of lubricating composition deposited in step a) may be within the range of from 0.001 to 1 g/cm$^2$, such as within the range of 0.01 to 0.1 g/cm$^2$, or such as within the range of from 0.01 to 0.05 g/cm$^2$.

In an embodiment, the layer of lubricating composition in step a) is topically deposited.

In an embodiment, the lubricating composition comprises silicone. The lubricating composition may for example further comprise oils, fats, soaps, humectants, moisturizers, grease and/or lubricants.

In an embodiment, the lubricating composition comprises silicone to an amount of at least 5% by weight of the total composition. In an embodiment of this aspect, the lubricating composition comprises silicone to an amount within the range of from 20 to 30% by weight of the total composition. In an embodiment of this aspect, the lubricating composition comprises silicone to an amount of about 25% by weight of the total composition.

In an embodiment, the lubricating composition comprises silicone to an amount within the range of from 5 to 90% by weight of the total composition, such as within the range of from 5 to 80% by weight of the total composition, or such as within the range of from 15 to 80% by weight of the total composition. In another embodiment, the lubricating composition comprises silicone to an amount within the range of from 20 to 60% by weight of the total composition, such as within the range of from 20 to 50% by weight of the total composition. In an embodiment, the support is human skin.

There is in a further aspect provided a lubricating composition for use in the method according to the present invention.

The objects of the invention are moreover achieved, in a further aspect, by the use of a layer of a lubricating composition on a support for lubricating an injection needle when used multiple times at a single occasion to penetrate the layer.

The use thus provides an improved and simplified process, in which the use of the lubricating composition enables the injection needle to be efficiently lubricated when it is used multiple times a single occasion. The same advantages which apply to the method and which are described above also apply to the use aspect of the present invention.

Further embodiments disclosed in relation to the method aspect of the present invention are also relevant for the use aspect of the present invention.

The objects of the invention are moreover achieved, in a further aspect, by a kit comprising:

a) an injection needle;
b) a lubricating composition for lubricating the injection needle when used multiple times according to the method of the present invention.

Advantages previously presented regarding the method for lubricating an injection needle when used multiple times, the lubricating composition for use in the method and for the use of a layer of lubricating composition, also apply to the kit comprising a) and b).

The objects of the invention are moreover achieved, in a further aspect, by a method of preparing the skin of a human patient for multiple penetrations with an injection needle at a single occasion, the method comprising the step of depositing a layer of a lubricating composition on the skin prior to the penetrations.

Advantages of the method of preparing the skin of a human patient for multiple penetrations with an injection needle at a single occasion may be that an overall faster treatment time of the patient may be achieved. Hence, the treatment would be more time-efficient which may e.g. lead to a greater economical win.

Advantages previously presented regarding the method for lubricating an injection needle when used multiple times, the lubricating composition for use in the method and for the use of a layer of lubricating composition, also apply to the method of this aspect.

In an embodiment, there is a method for injecting multiple doses of an injectable composition into human skin at a single occasion, the method comprising the steps of:

a) depositing a layer of a lubricating composition on the skin,
b) penetrating multiple times the layer of the lubricating composition deposited in step a) and the skin with the injection needle, thereby providing a lubricated injection needle having a deposited layer of the lubricating composition thereon; and
c) injecting a dose of the injectable composition each time the injection needle penetrates the skin.

Similar to the advantages described above for the inventive method, the method of injecting multiple doses of the injectable composition into human skin at a single occasion, also provides an improved and simplified process, in which the injection needle is efficiently lubricated when it is used multiple times at a single occasion. Hence, the injection needle may acquire a deposited layer of the lubricating composition thereon, such as each of the multiple times it is used. The injection needle thus becomes re-lubricated each of the multiple times it is used.

In this embodiment, the method comprises the step c) of injecting a dose of the injectable composition each time the injection needle penetrates the skin. The step c) may be performed immediately subsequent to step b), thereby providing an injection needle which is efficiently lubricated prior to penetrating the skin and prior to injecting the injectable composition therein. Hence, the injection needle may efficiently be lubricated, while performing the method steps b) and c), each of the multiple times the injection needle is used.

Thus, in an embodiment, steps b) and c) are performed at least 10 times, or even more than 10 times, such as at least 15 times. In an embodiment, steps b) and c) are performed at least 5 times, such as at least 7 times or such as at least 9 times. In an embodiment, steps b) and c) are performed at least 12 times, such as at least 17 times or such as at least 20 times. In an embodiment, steps b) and c) are performed at least 30 times, such as at least 40 times or such as at least 50 times. In an embodiment, steps b) and c) are performed at least 70 times, such as at least 100 times or such as at least 130 times. In an embodiment, steps b) and c) are performed at least 150 times, such as at least 170 times or such as at least 200 times.

An advantage of the injection needle being efficiently lubricated is that the injection needle may have a prolonged life time and may thus be used multiple times at a single occasion without having to exchange the injection needle for a new injection needle while performing the method steps a) to c). Thus, the method in this embodiment may save time and may therewith be performed in a more time-efficient way. Thus, the method in this embodiment may also be more economical due to the method being time-efficient. Moreover, a further benefit of not having to exchange the injection needle as often is that there is a reduced risk of the treating professional accidentally injuring him- or herself with the injection needle before, during and/or after treatment. Hence the method of the present invention contributes to an increased safety.

Further, since there is no need to discharge the needle in-between the multiple times it is used it thus leads to a more economical and environmentally friendly way of using the injection needles.

By keeping the injection needle lubricated, according to the method of this embodiment, it may not be experienced that the injection needle turns blunt. Therefore, there is a decreased need to significantly increase the force performed on the injection needle in order for it to penetrate the skin, since the required penetration force is kept lower than compared to when conventional injection needles are used multiple times without any lubrication between the penetrations. Since the required penetration force is kept low, the method of this embodiment makes it easier for to timely decrease the pressure that is acting on the syringe as the injection needle penetrates the skin. Hence, this method may provide a more controlled way in which multiple doses of an injectable composition is injected into human skin at a single occasion. The described method according to this embodiment may further offer a safer method for injecting multiple doses into the human skin.

The deposited layer of lubricating composition on the injection needle may further result in that the injection needle easier penetrates the skin.

The injectable composition may for example comprise silicone. Embodiments disclosed in relation to the inventive method of the present invention are also relevant for the method in this embodiment.

The lubricating composition used in the method of this embodiment may reduce the penetration force, such as a penetration force $F_2$, relating to when the support is dilated and/or such as a penetration force $F_R$, relating to when the shaft of the injection needle passes through the support and thereby the force needed to penetrate the support.

Referring now to the Figures, which are exemplary embodiments, wherein.

In order to provide improved and simplified solutions for the use of an injection needle multiple times at a single occasion, it has been found important to efficiently maintain the injection needle lubricated.

Figure 1:
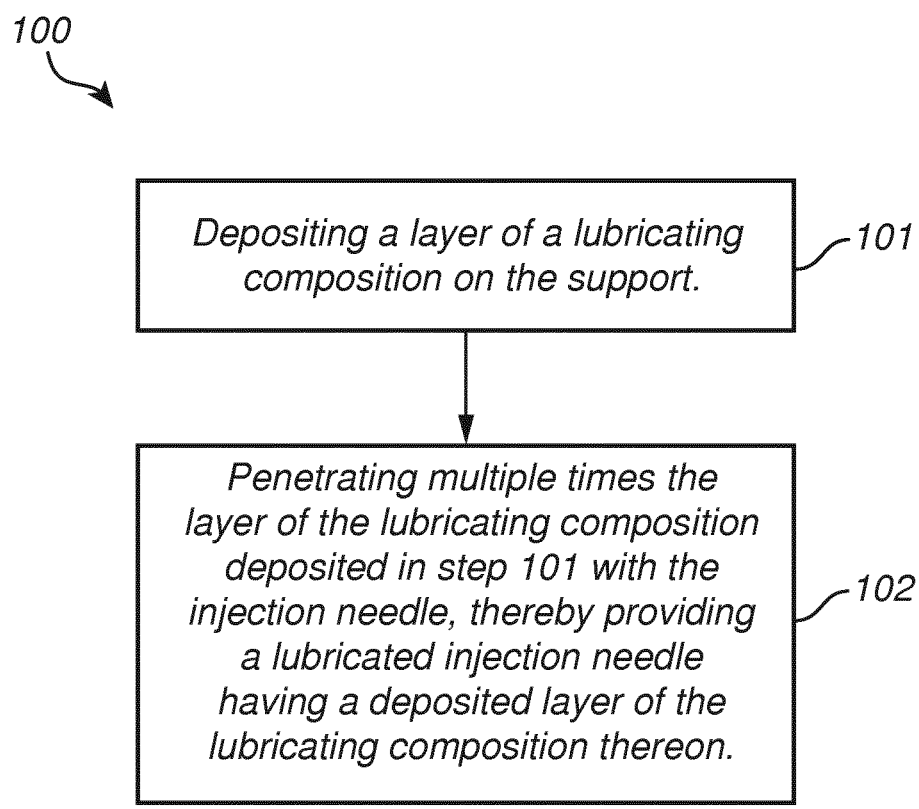
FIG. 1 is a flow chart depicting one example of a method for lubricating an injection needle when used multiple times.

FIG. 1 is a flow chart of a method 100 for lubricating an injection needle when used multiple times at a single occasion to penetrate a support according to one embodiment of the present invention. In a first step 101, a layer of a lubricating composition is deposited on the support. Thereafter, the layer of the lubricating composition deposited in step 101 is penetrated multiple times with the injection needle, thereby providing a lubricated injection needle having a deposited layer of the lubricating composition thereon.

The term "injection needle", should herein be understood as a hollow needle or a solid needle intended to be used with a syringe to penetrate a lubricating composition, such as in the direction of the support. The injection needle is usually made of stainless steel.

The term "lubricating composition", should herein be understood as any composition which is lubricating. The lubricating composition may reduce friction between two, in relation to each other, moving surfaces. The lubricating composition may be sterilisable. A preferred lubricating composition is a skin lotion, cream or gel, optionally containing silicone.

The term "single occasion", should herein be understood as an occasion, limited in time, which occurs once, wherein the injection needle may be used for penetration multiple times. A typical treatment occasion will last for 1 to 60 min, such as 1 to 15 min.

An injection needle, which is intended to be used once, may according to the invention be used for penetration multiple times. The injection needle may further in the inventive method be efficiently re-lubricated each of the multiple times the injection needle is used for penetration. In the inventive method, a conventional injection needle, such as the injection needle intended to be used once, may be used multiple times. Hence, the inventive method enables reuse of the injection needle.

In the prior art method presented in the background of the invention, a specific apparatus has been suggested for e.g. lubricating the injection needle. In the inventive method, there is no need for such a special apparatus for lubricating the injection needle since the present invention inventively involves a simplified way of lubricating the injection needle. There is further in the present invention no need for any temporary storage of the injection needle in-between each of its multiple uses, at a single occasion, for lubricating the injection needle.

The layer of the lubricating composition may, in step 101, be topically deposited on the support.

The injection needle may be a hypodermic needle. The injection needle may also be a solid needle.

Figure 2:
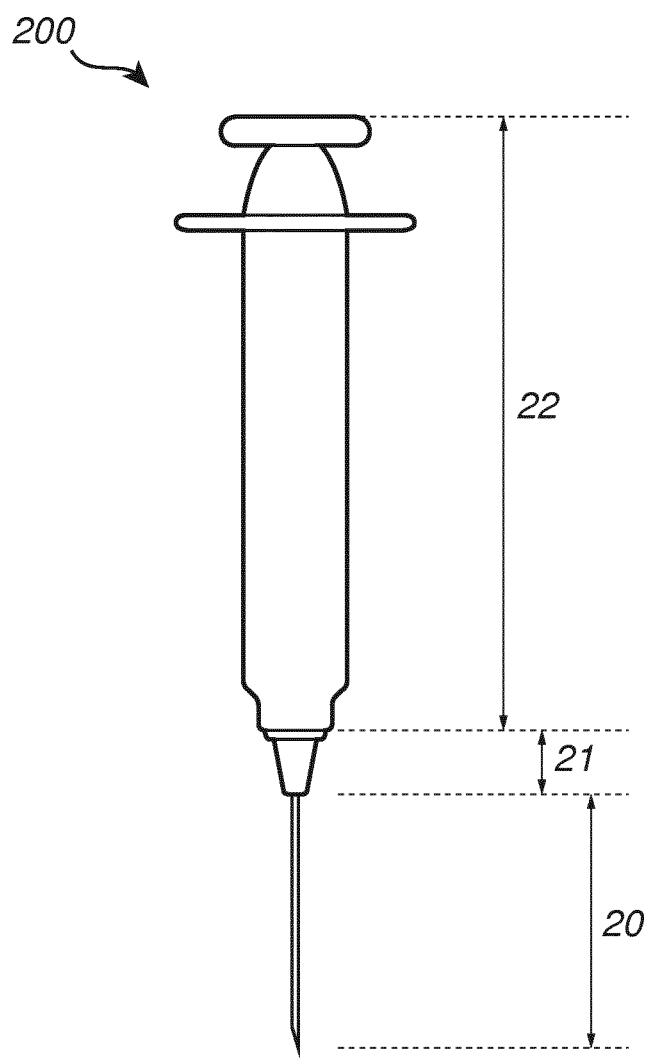
FIG. 2 is a schematic view of a syringe having an injection needle.
Figure 3:
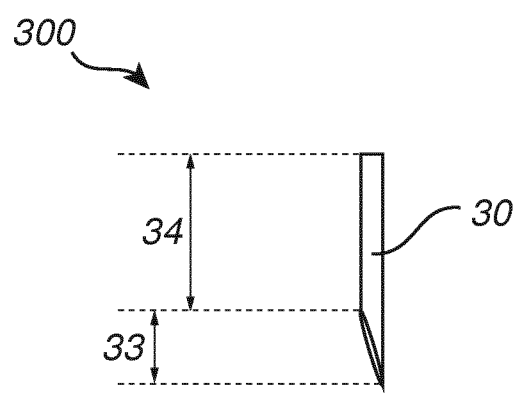
FIG. 3 is a schematic view of an injection needle.

Another exemplary embodiment will now be described with reference to FIG. 2. FIG. 2 shows an injection device 200 comprising an injection needle 20, which may be reversibly interconnected by a Luer taper connection 21 to a syringe 22. An enlargement of the injection needle is seen in FIG. 3. The injection needle 30 comprises a cutting edge 33 and a hollow shaft 34. A preferred needle has two grinding angles (so-called facette grinding), i.e. four surfaces.

Figure 4:
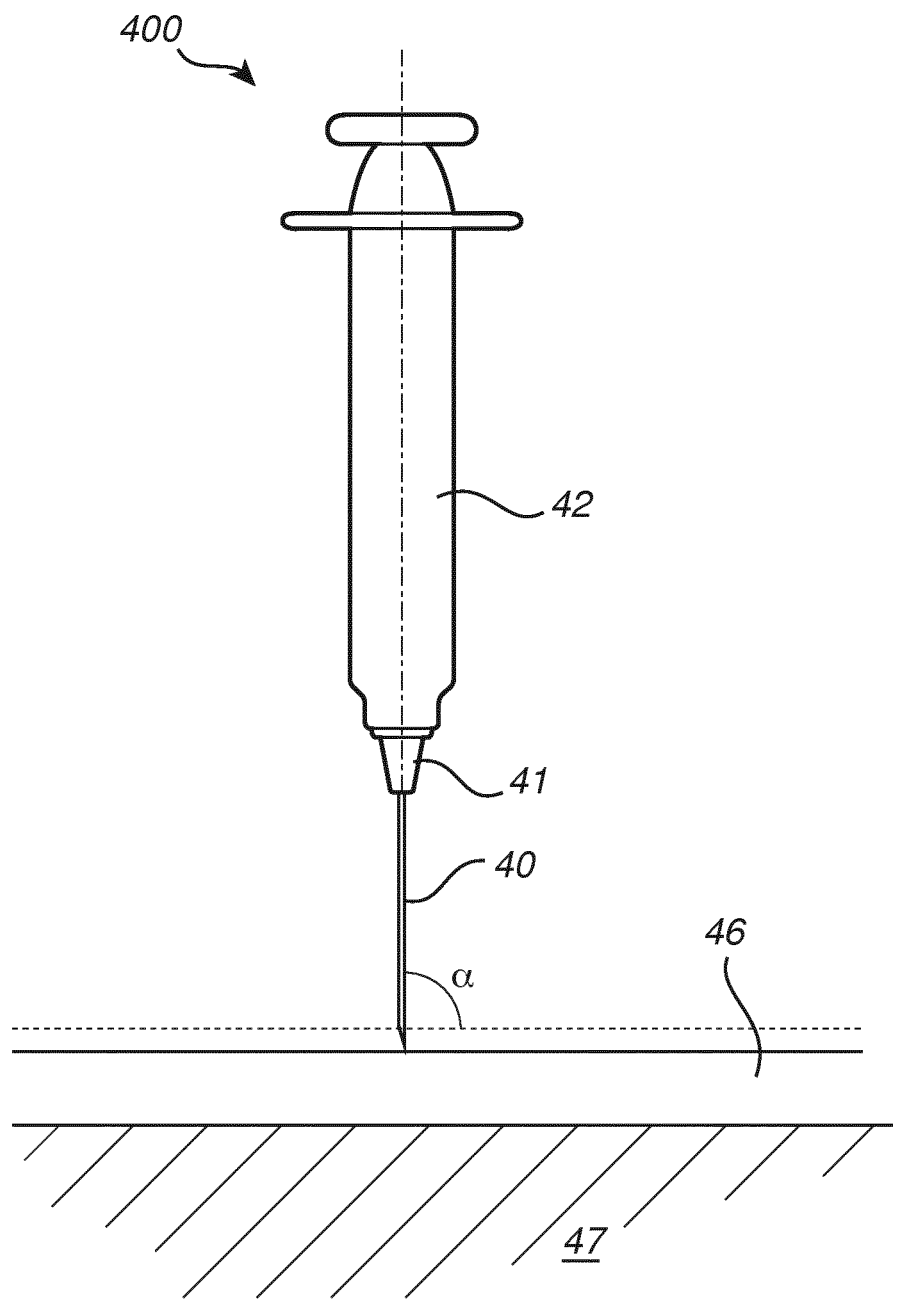
FIG. 4 is a cross-sectional view of a syringe directed towards a deposited layer of a lubricating composition on a support.

Another exemplary embodiment will now be described with reference to FIG. 4. FIG. 4 shows an arrangement 400 of the method for lubricating the injection needle when used multiple times at a single occasion. FIG. 4 is a cross-sectional side view of a syringe directed towards a deposited layer of a lubricating composition 46 on a support 47. The layer is deposited on the support with an amount of the lubricating composition within the range of from 0.001 to 1 $g/cm^2$, such as within the range of 0.01 to 0.1 $g/cm^2$, or such within the range of from 0.01 to 0.05 $g/cm^2$. The injection device 200 having an injection needle 40, reversibly interconnected by the Luer taper connection 41 to the syringe 42 is illustrated in the direction towards the support. By moving the injection device 200 in the direction towards the support, the injection needle may penetrate the layer of the lubricating composition 46, thereby providing a lubricated injection needle having a deposited layer of the lubricating composition 46 thereon, such as each of the multiple times the injection needle 40 is used. Although, the injection device 200 is illustrated substantially perpendicular to the layer of the lubricating composition 46, the injection device 200 may penetrate the layer of the lubricating composition with an angle α smaller than 90°, the angle being defined between the injection device 200 and the lubricating composition 46 as long as the first layer to be penetrated by the injection needle 40 is the layer of lubricating composition 46.

Figure 5:
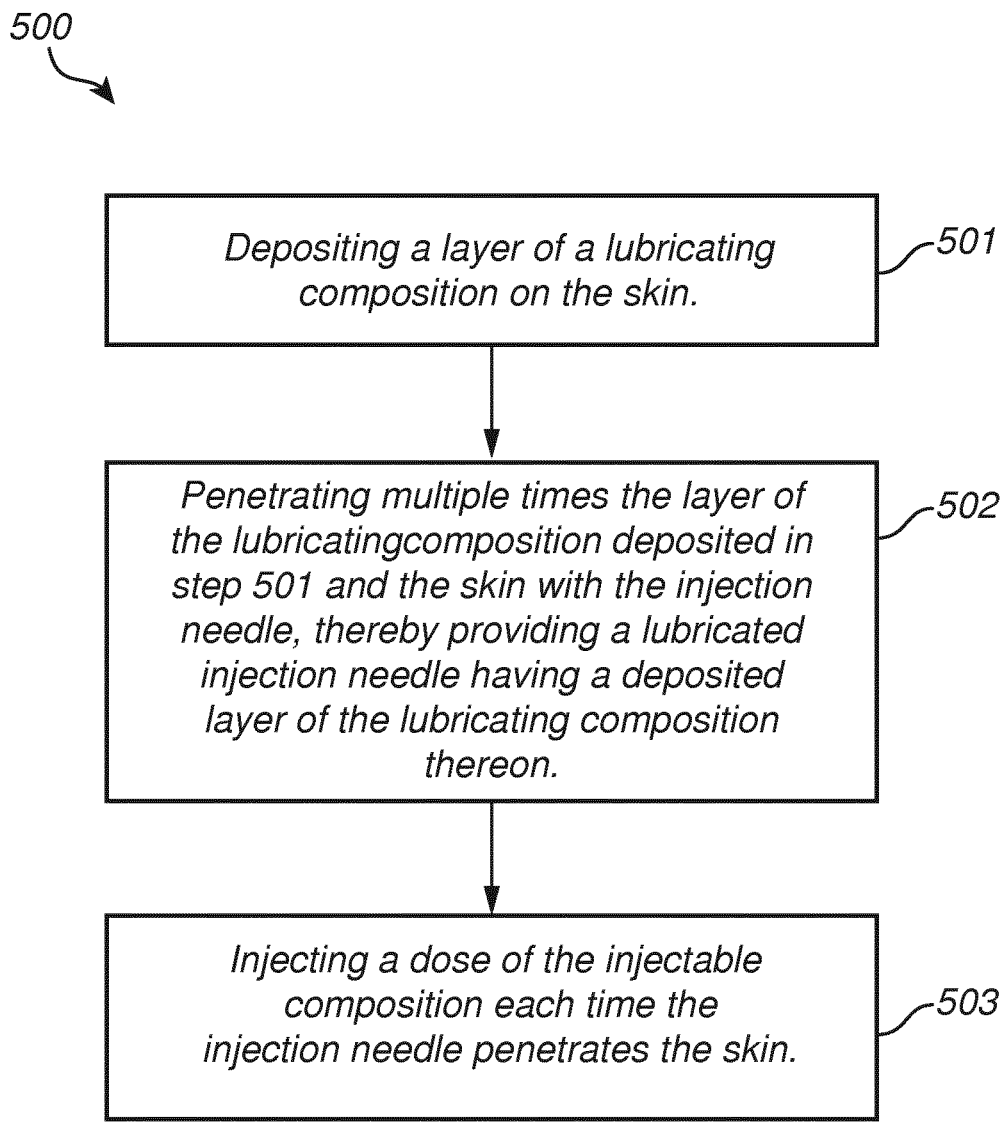
FIG. 5 is a flow chart depicting one example of a method for injecting multiple doses of an injectable composition into human skin at a single occasion.

Another exemplary embodiment will now be described with reference to FIG. 5. FIG. 5 is a flow chart of a method 500 for injecting multiple doses of an injectable composition into human skin at a single occasion according to an embodiment of the present invention. In a first step 501, a layer of a lubricating composition is deposited on the skin. Thereafter, the layer of the lubricating composition deposited in step 501 and the skin is, in a further step 502, penetrated multiple times with the injection needle, thereby providing a lubricated injection needle having a deposited layer of the lubricating composition thereon, such as each of the multiple times the injection needle is used. Step 502 is followed by step 503 of injecting a dose of the injectable composition each time the injection needle penetrates the skin.

The term "injectable composition", should herein be understood as any composition which may be injectable through or via the injection needle into a support. The injectable composition may be a filler and/or a toxin composition.

The filler may for example be hyaluronic acid. Hyaluronic acid refers to a compound constituted of series of glucuronic acid and of N-acetylglucosamine. Hyaluronic acid can be in the form of a pharmaceutically acceptable salt or derivatives thereof, particularly a sodium or potassium salt. Hyaluronic acid may be used in various forms: a salt, a derivative such as an ester or an amide. Hyaluronic acid may be in a linear or in a cross-linked form. When the hyaluronic acid is in its cross-linked form, the hyaluronic acid's individual chains are chemically bound (or cross-linked) together into a soft solid, or gel. The strength or firmness of the gel depends on the degree of cross-linking of the individual acid chains.

Another filler may for example be collagen. Further examples of the filler may be poly acrylamide, calcium hydroxyl apatite, poly lactide acid, poly (methyl metacrylate).

An example of the toxin is botulinum toxin, which herein refers to a botulinum neurotoxin produced by *Clostridium botulinum* or *Clostridium baratii*, as well as a botulinum toxin, or the light chain or the heavy chain thereof which are subsequently combined together, made by genetic recombinant techniques using a non-Clostridial species. Botulinum toxin herein encompasses the botulinum toxin serotypes A, B, C, D, E, F and G and their subtypes. Botulinum toxin also encompasses both a botulinum toxin complex, i.e. the complexes of approximate molecular weight 300, 600 and 900 kDa or other complexes as produced naturally by the bacteria, as well as purified botulinum toxin, having approximately 150 kDa in molecular weight. The purified botulinum toxin is a botulinum neurotoxin that is isolated, separated or substantially isolated or separated, from other proteins. The botulinum toxin further encompasses modified botulinum toxin, which is a botulinum toxin that has at least one of its amino acids deleted, modified, or replaced, as compared to native botulinum toxin.

The skin comprises three layers, which knowingly to the person skilled in the art are; epidermis, the outermost layer of the skin, dermis, the layer beneath epidermis, and the deeper subcutaneous tissue or hypodermis, the layer beneath both epidermis and dermis. The penetration of the skin in step 503, in order to inject a dose of the injectable composition, may be minimal invasive, such as the injection needle may penetrate the epidermis and may further penetrate into the layer of dermis. The deeper subcutaneous tissue or hypodermis may not be reached by the injection needle nor penetrated by the injection needle according to the present invention.

The thickness of the epidermis and dermis of the skin may vary in different parts of the skin of the human body. The epidermis may for example have a thickness of 0.05 mm in the eyelids and a thickness of 1.5 mm in the palms and soles. The thickness of the dermis may also vary in different parts of the human body. The dermis may for example have a thickness of 0.3 mm in the eyelids and a thickness of 1.5 mm in the palms and soles. Hence, the penetration depth of the injection needle is shallow. Due to the different thicknesses of the epidermis and dermis of the skin, the injection needle may penetrate to a penetration depth, which varies depending on where on the human body the injectable composition is injected. The penetration depth further varies depending on the angle α with which the injection device 200 is penetrating the skin.

"Penetration depth" is herein referred to as a measure of how deep the injection needle may penetrate through the lubricating composition and into the support, in order to reach dermis of the skin. The penetration depth of the injection needle may vary depending on the length of the injection needle and depending on the inclination, i.e. the angle α, of which the injection needle penetrates into the skin. If the injection needle penetrates the skin almost horizontally, the penetration depth may be within the range of from 1 to 50 mm and if the injection needle penetrates the skin almost vertically, the penetration depth may be within the range of from 1 to 10 mm.

The dose of the injectable composition may be injected into epidermis or dermis of the skin. The dose of the injectable composition may preferably be injected into dermis of the skin. The dose of the injectable composition may be injected into dermis of for example the eyelid, lip, forehead, palm, backhand, sole of feet and/or armpit.

The method according to the invention is particularly useful in cosmetic treatment, e.g. for multiple administrations of the injectable composition into the skin without any medical risk for the treated subject.

The method according to the invention may also be useful in medical treatments, in particular involving botulinum toxin.

EXAMPLES

Aim of Test

The inventors investigated how the lubricating composition affected the penetration force acting on the injection needle when used multiple times at a single occasion. The penetration forces measured were the penetration force $F_2$ and the penetration force $F_R$.

Principle of an Injection Needle Penetration Measurement

Figure 6:
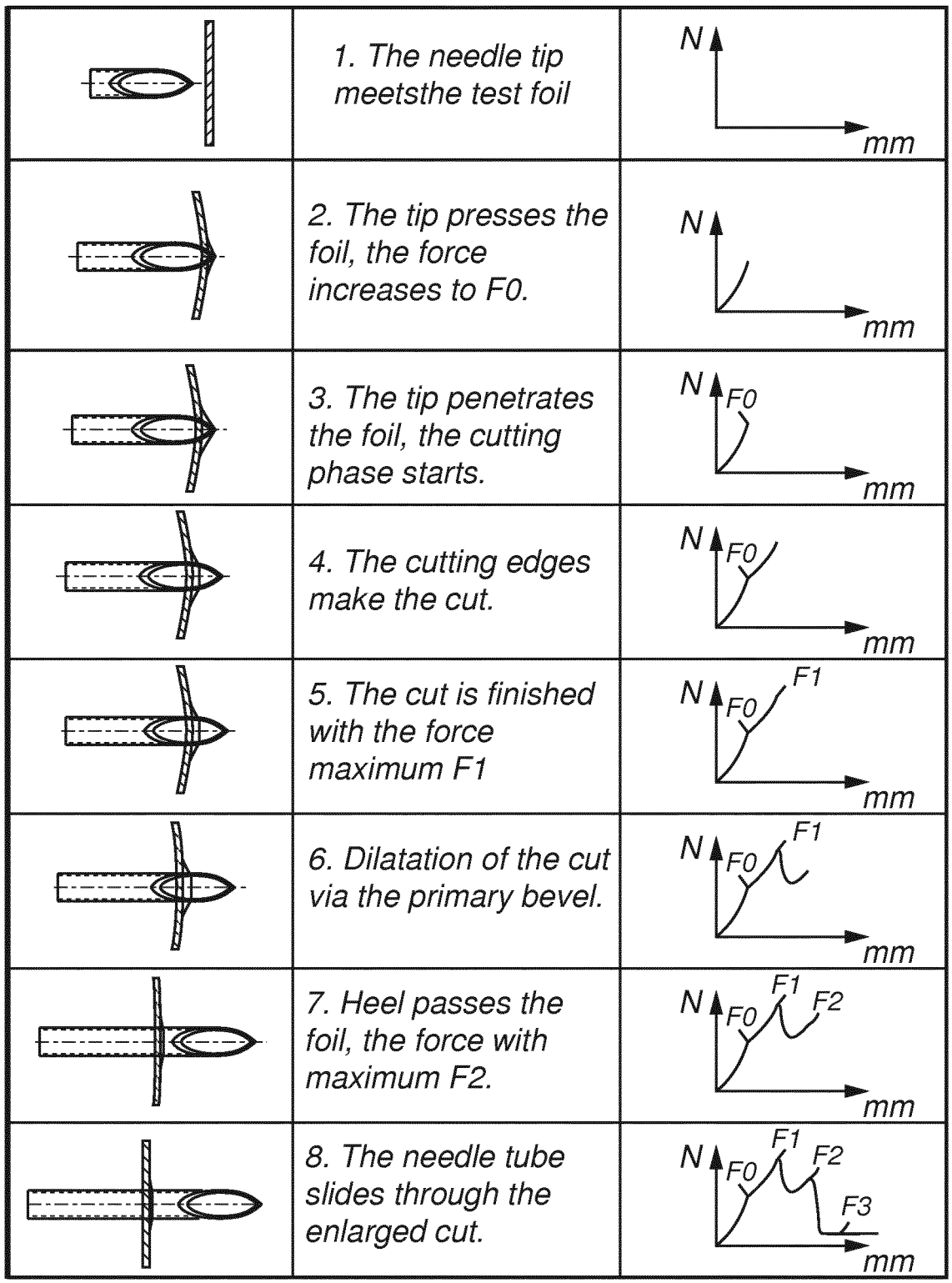
FIG. 6 is a table describing a standard test of an injection needle penetrating a support (http://www.iso.org/iso/catalogue_detail.htm?csnumber=58079).

FIG. 6 is a table describing a standard test (ISO/DIS 11040-4) of an injection needle penetrating a support. The penetration force $F_0$ represents when a needle tip of the injection needle penetrates a test foil. The penetration force $F_1$ represents when the cutting edge of the injection needle passes through the test foil. The penetration force $F_2$ represents when the test foil is dilated, i.e. when the heel passes the foil. The penetration force $F_3$, i.e. $F_R$, represents when the shaft of the injection needle penetrates the test foil.

Materials

The following chemicals as well as materials and equipment were used in the tests.

Chemicals

Skin cream base: ACO Body skinlotion, unscented, art no 100561 from ACO HUD NORDIC AB (SE-Upplands Väsby). The skin cream base comprises aqua, paraffin liquid, glycerine, isopropyl myristine, parraffin, glyceryl stearate citrate, glyceryl stearate, cetearyl alcohol, acrylates/C10-30 alkyl acrylate, crosspolymer, xantham gum, sodium hydroxide phenoxyethanol, potassium sorbate and sodium benzoate.

Silicone, DC 360, 1000 CST.

Materials and Equipment

Test foil: DEKATEST PU 0.08 mm/width 80 mm/length 1.000 mm from Melab, lot 271009.

Injection needle with facette grinding: Terumo Europe N.V., 29G×½" TW (0.33×12 mm), Belgium, lot 1202010.

Skin Pad: Q-Med training skin pad 15-77375.

Test equipment: Custom made equipment based on the syringe pump ProSense B.V. Model number NE-1000 and serial number 245238/17668+load cell. Speed: 352.5 µm/s.

Mixing equipment for mixing skin cream base with silicone: Polytron 10-35 GT, homogenizer.

Test Method

1. Preparation of a Lubricating Composition

Firstly, five different lubricating compositions were prepared. Three of the lubricating compositions were prepared by mixing the skin cream base with silicone to a ratio of skin cream base vs. silicone, having 95/5, 75/25, and 50/50, respectively. The remaining two lubricating compositions were left unmixed, 100/0, i.e. 100% skin cream base and 0/100, i.e. 100% silicone, respectively.

2. Depositing the Lubricating Composition on a Support

Thereafter the five different lubricating compositions were deposited, as a layer of the lubricating composition, on different supports, i.e. skin pads, thereby achieving five prepared skin pads, each of them having a different prepared lubricating composition thereon. The lubricating composition was deposited on each of the skin pads to a layer thickness of the lubricating composition of 0.03 g/cm². One skin pad was left without any lubricating compositions and used as a reference in the test.

3. Penetrating a Prepared Skin Pad with an Injection Needle

Referring now to the skin pad having a deposited layer of 100% skin cream base (100/0), an injection needle, according to the above referenced model, penetrated once, in the direction of the skin pad, firstly the deposited lubricating composition, thereby providing a lubricated injection needle having a deposited layer of the lubricating composition thereon, and secondly the skin pad. A penetration is herein referred to as penetrating in two directions, firstly into the skin pad and secondly out of the skin pad, passing the lubricating composition twice.

4. Measuring a Penetration Force Acting on the Injection Needle

Subsequent to the first penetration of the injection needle through the lubricating composition of 100% skin cream base (100/0) and into the skin pad, the injection needle was mounted on the test equipment, presented above, to measure its penetration force. While recording the penetration force, the injection needle was let to penetrate a test foil, according to the above referenced test foil, made of an elastic plastic film of polyurethane film having a thickness of 0.08 mm.

5. Repeating the Penetration and Measuring Step of a First Test Series

After the measure of the penetration force acting on the injection needle, which had penetrated the skin pad having 100% skin cream base thereon, the injection needle was once again let to penetrate the skin pad having the deposited layer of 100% skin cream base. Thereafter the penetration force of the injection needle was once again measured according to step 4.

The step 3 and 4 were repeated and the penetration force was measured after the $3^{th}$, $4^{th}$, $5^{th}$, $10^{th}$, $25^{th}$ and $50^{th}$ penetration in the skin pad, respectively, thereby achieving a test result from a first test series.

The repeatability of the test method was tested by testing a skin pad having the same layer of lubricating composition deposited thereon for another two test series á 50 penetrations according to step 3 to 5. In the beginning of each test series, a new injection needle was used.

6. Testing the Remaining Skin Pads, Prepared in Step 1 and 2

The same test procedure and penetration force measurement, as in step 3 to 5, were performed with the skin pads each having lubricating composition ratios of skin cream base vs. silicone of 95/5, 75/25, and 50/50, as well as 100% silicone and to the skin pad without having any lubricating composition, i.e. the reference skin pad.

Results

The penetration force measured in the tests was the penetration force $F_2$ and the penetration force $F_R$ ($F_3$) as depicted in FIG. 6. The penetration force $F_2$ acts, in the direction towards the cutting edge of the injection needle when the cutting edge is penetrating the support, i.e. when the support is dilated. The penetration force $F_R$ acts, in the direction along the shaft, in the opposite direction of the penetration direction, on the injection needle.

Figure 7:
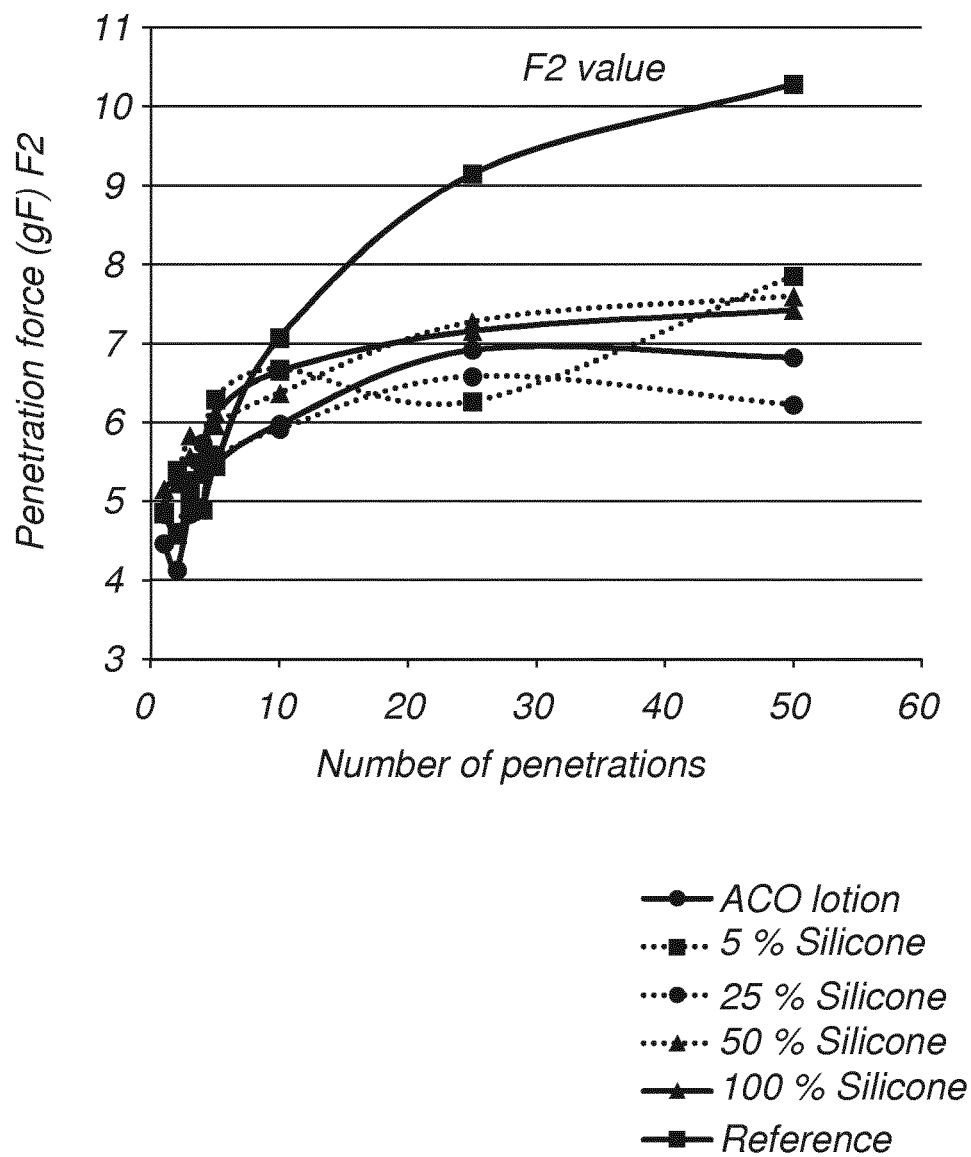
FIG. 7 is a graph illustrating the penetration force $F_2$ of the injection needle after it had been used multiple times.

FIG. 7 is a graph illustrating how the penetration force $F_2$, measured on an injection needle, is changing with an increased number of penetrations into a skin pad. FIG. 7 shows six curves showing penetration force measurements of the penetration force $F_2$, from six different injection needles, each of which have penetrated the prepared skin pads of step 2 above, i.e. 0/100, 50/50, 75/25, 95/5, 100/0 (skin cream base/silicone), and the reference skin pad without any deposited lubricating composition.

As can be seen in FIG. 7, after 10 penetrations, the injection needles which had penetrated the lubricated skin pads, i.e. 0/100, 50/50, 75/25, 95/5 and 100/0, are all showing a lower penetration force $F_2$ compared to the injection needle which has penetrated the reference skin pad, i.e. without any lubrication. An effect may be seen at even lower numbers of penetrations, for example of the penetration force $F_2$, of the injection needles which have penetrated the 100/0 and the 75/25 samples. 75/25 shows the lowest penetration force $F_2$ overall and after 50 penetrations.

Figure 8:
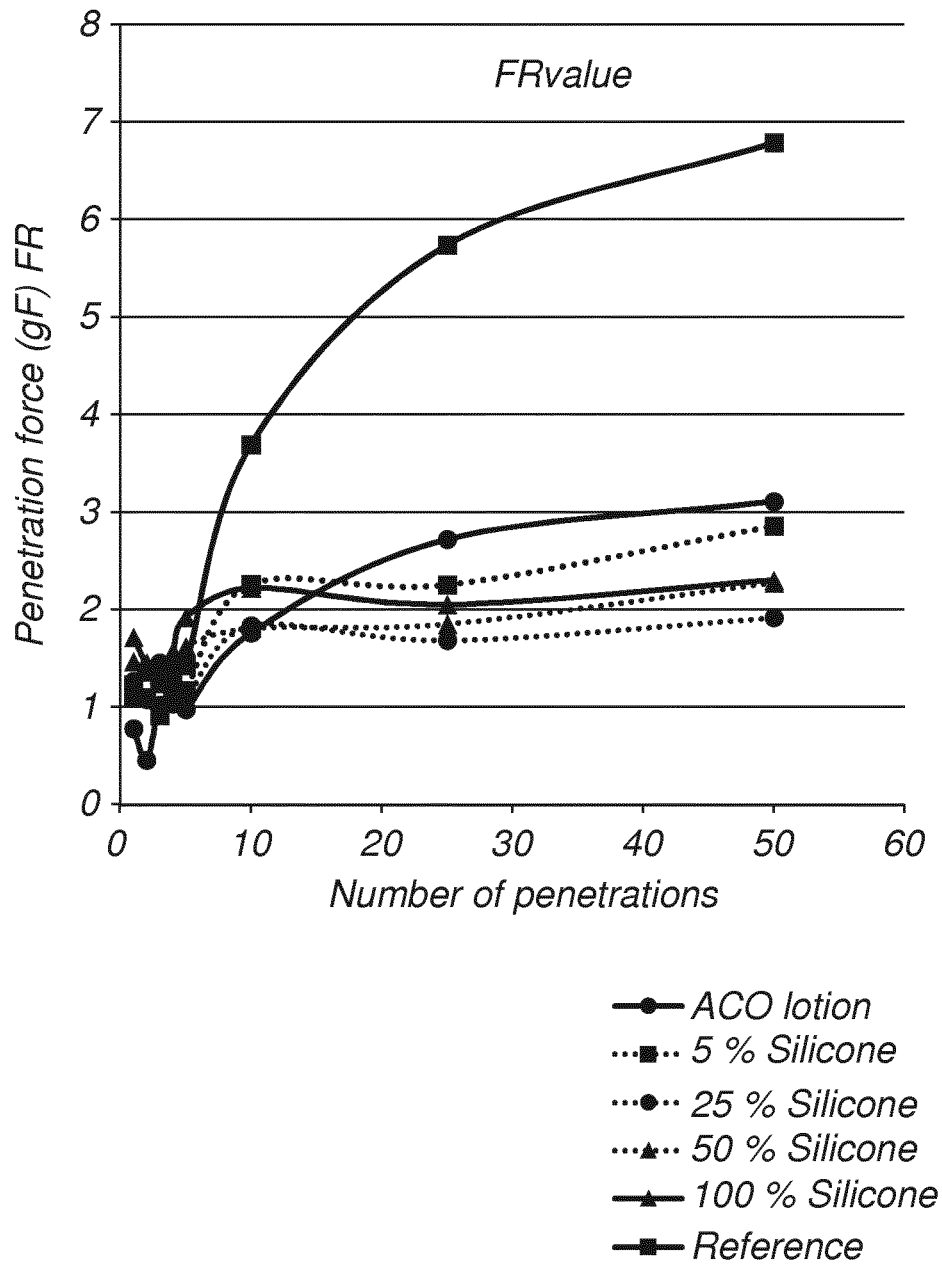
FIG. 8 is a graph illustrating the penetration force $F_R$ of the injection needle after it had been used multiple times.

FIG. 8 is a graph illustrating how the penetration force $F_R$, measured on an injection needle, is changing with an increased number of penetrations into a skin pad. FIG. 8 shows six curves showing penetration force measurements of the penetration force $F_R$ from six different injection needles, each of which have penetrated the prepared skin pads of step 2 above, i.e. 0/100, 50/50, 75/25, 95/5, 100/0 (skin cream base/silicone), and the reference skin pad.

As can be seen in FIG. 8, after 10 times used, the injection needles which had penetrated the lubricated skin pads, i.e. 0/100, 50/50, 75/25, 95/5 and 100/0, are all showing a lower penetration force, $F_R$, compared to the injection needle which has penetrated the reference skin pad, i.e. without any lubrication. It is noticeable that all compositions containing silicone provided a lower penetration force, $F_R$, than the composition without silicone above 10 penetrations. 75/25 shows the lowest penetration force, $F_R$, overall and after 50 penetrations.

CONCLUSION

By depositing a layer of a lubricating composition, according to the invention, on a skin pad, the penetration force ($F_2$, $F_R$) is significantly reduced when an injection needle is used multiple times for penetration at a single occasion.

The invention claimed is:

1. A method for lubricating an injection needle when used multiple times at a single occasion to penetrate a human skin support, the method comprising:
    a) depositing a layer of a lubricating composition on the human skin support; and
    b) penetrating multiple times in a single occasion the layer of the lubricating composition deposited in step a) with an injection needle, thereby providing a lubricated injection needle having a deposited layer of the lubricating composition thereon, the number of times being more than 30, but less than or equal to 50,
    wherein the injection needle is lubricated after each of the multiple times in the single occasion so as to maintain lubrication of the injection needle during the single occasion,
    wherein the lubricating composition comprises silicone, and
    wherein the lubricating composition comprises silicone in an amount within the range of from 25% to 30% by weight of the total composition.

2. The method according to claim 1, wherein step a) is performed once.

3. The method according to claim 1, wherein step b) is performed at least 10 times.

4. The method according to claim 1, wherein the lubricating composition is sterile.

5. The method of claim 1, wherein an amount of lubricating composition deposited on the human skin support is within the range of 0.01 g/cm² to 0.1 g/cm².

6. The method of claim 1, wherein the injection needle is lubricated after each of the multiple times in the single occasion so as to re-lubricate the needle multiple times.

7. The method of claim 1, wherein:
    the lubricating composition is penetrated prior to penetration of the human skin support, such that the lubricating composition is a first layer penetrated by the injection needle and the human skin support is a second layer penetrated by the injection needle.

8. The method of claim 7, wherein a penetration angle between the injection needle and the lubricating composition is smaller than 90°.

9. The method of claim 1, wherein the injection needle comprises a cutting edge and a hollow shaft.

10. The method of claim 9, wherein:
    when the injection needle is penetrating into the human skin support, a first penetration force acts in a first direction toward the cutting edge when the human skin support is penetrated by the cutting edge, and a second penetration force acts in a second direction along the hollow shaft and opposite to the first direction.

11. The method of claim 1, wherein the injection needle comprises two grinding surfaces.

12. The method of claim 1, wherein the lubricating composition comprises silicone in an amount of 25% by weight of the total composition.

13. A method for injecting multiple doses of an injectable composition into human skin at a single occasion, the method comprising:
    a) depositing a layer of a lubricating composition on the skin;
    b) penetrating multiple times in a single occasion the layer of the lubricating composition deposited in step a) with an injection needle, thereby providing a lubricated injection needle having a deposited layer of the lubricating composition thereon, the number of times being more than 30, but less than or equal to 50; and
    c) injecting a dose of the injectable composition each time the injection needle penetrates the skin,
    wherein the injection needle is lubricated after each of the multiple times in the single occasion so as to maintain lubrication of the injection needle during the single occasion,
    wherein the lubricating composition comprises silicone, and
    wherein the lubricating composition comprises silicone in an amount within the range of from 25% to 30% by weight of the total composition.

14. The method according to claim 13, wherein the injectable composition is selected from a filler and a toxin composition.

15. The method according to claim 14, wherein the injectable composition is a filler composition containing a filler selected from hyaluronic acid and derivatives thereof, in linear or cross-linked form, collagen, poly acrylamide, calcium hydroxyl apatite, poly lactide acid, and poly (methyl metacrylate).

16. The method according to claim 15, wherein the filler is cross-linked hyaluronic acid.

17. The method according to claim 14, wherein the injectable composition is a toxin composition containing botulinum toxin.

18. The method according to claim 13, wherein the method is a cosmetic treatment method.

19. The method of claim 13, wherein the lubricating composition comprises silicone in an amount of 25% by weight of the total composition.

* * * * *